United States Patent [19]

Nakamura et al.

[11] Patent Number: 4,510,699

[45] Date of Patent: Apr. 16, 1985

[54] INSOLE

[75] Inventors: Toshiro Nakamura, 132, Omori-cho-ha, Oda-shi, Shimane 694-03; Tetsuya Watanabe, Oda, both of Japan

[73] Assignee: Toshiro Nakamura, Oda, Japan

[21] Appl. No.: 437,300

[22] Filed: Oct. 28, 1982

[30] Foreign Application Priority Data

Oct. 26, 1981 [JP] Japan .......................... 56-195741[U]
Oct. 29, 1981 [JP] Japan .......................... 56-162981[U]
Mar. 30, 1982 [JP] Japan ................................. 57-52709

[51] Int. Cl.³ ...................... A43B 13/40; A43B 13/38
[52] U.S. Cl. .......................................... 36/43; 36/71; 128/614
[58] Field of Search ................................. 36/43, 44, 71; 128/80 D, 153, 166.5, 586, 588, 611, 615, 614, 582, 602, 591

[56]  References Cited

U.S. PATENT DOCUMENTS

| 982,664 | 1/1911 | Fischer | 128/80 D |
| 2,021,467 | 11/1935 | Rosenthal | 128/614 |
| 2,454,836 | 11/1948 | Rayner | 128/80 D |
| 3,555,706 | 1/1971 | Edmonds | 36/71 |
| 3,722,113 | 3/1973 | Birkenstock | 128/582 |
| 3,828,792 | 8/1974 | Valenta | 128/614 |

FOREIGN PATENT DOCUMENTS 1258923 3/1961 France ............................ 128/611

Primary Examiner—Werner H. Schroeder
Assistant Examiner—Steven N. Meyers
Attorney, Agent, or Firm—Darby & Darby

[57] ABSTRACT

An insole the material for which is made from a elastomer showing gum-like elasticity under the normal temperature, and which is provided with a wedge-shaped profile, irregularities, curves, and the like for the purpose of making the sole incline or correcting the state of unevenness thereof. It is used by being inserted inside shoes, slippers, sandals, etc., or by being worn on the sole of the foot with the aid of socks, simple holders or band bodies being molded integrally with the holders. Further, it may be made by utilizing a foam-formed body, or by boring small holes for air permeation therein for retaining warmth or making it light-weight.

7 Claims, 8 Drawing Figures

INSOLE

BACKGROUND OF THE INVENTION

This invention relates to an improved insole which is used for conservative treatment to correct diseases of the lower limbs such as, for example, bandy legs, knock knees, fat feet, gonarthritis deformans, metatarsalgia, hallux valgus, and others. The invention is also used to supplement a person's stature for reasons of beauty and is further used for the forced inclining of the sole during athletic activities.

Heretofore, insoles that were rigid have been used for these purposes. Accordingly, there have been used in making them hard or relatively hard materials such as metals, for example, aluminum, hard plastics, leathers, cork and others.

The insoles which have for their main body hard materials as mentioned above, however, not only are inclined to be made thick so as to be strong and maintain their form, but also they must be molded so as to lap the sole form-fittingly by being deeply curved at their brim, for example, as in FIG. 1, with the object of improving poor adhesion to the sole. As result, insoles of this type are bulky on the whole, and accordingly it is difficult or impossible to use them by inserting them into socks because of their poor fit therein, as well as doing damage thereto. They are also hard to be used even as spacers for slippers or sandals (especially, of a slip-on type). They are usually used by being inserted into shoes, otherwise held on the soles with the aid of special holder made of leathers or canvas. When using such holders, however, various problems occur so that the footwear becomes hard to put on, or the holding of it is troublesome, the feedling is not good in the state of being loaded, or they cause sweating, when stained they are not washable, and so on. Further, conventional holders on the market are awkward in use, do not move well with the sole of the foot, and are accompanied by a feeling of physical disorder, especially at the time of walking in the standing position, so that it takes a considerable number of days until the user accommodates himself to the loading of them. What is more, these holders have still a hygenic problem to be solved, namely the occurrence of an offensive smell of sweat and soil resulting from the contact with the skin, particularly in the case of an insole made of leather or cork.

Under these circumstances, however, in the case of the conservative treatment or correction of diseases of lower limbs, unlike the case of the temporal use for beauty or doing athletics, for example, skiing, it is required to load the insole habitually over a considerable period of time. Since the insole heretofore in use had these various defects, many patients would withdraw the loading of them arbitrarily in the middle of the treatment. (According to certain data, the patients of this sort amounted to more than 2% of the whole: "Clinical Orthopedic Surgery", Vol XVI, No. 7, pp. 65–672, July 1981.) Some of them tell of the inefficaciousness of this treatment, others complain of physical or mental pains.

BRIEF SUMMARY OF THE INVENTION

It is an object of this invention to provide an insole which has been enhanced in effectiveness in conducting the treatment of diseases at the regions of knees and soles by eliminating the above-mentioned defects of conventional insoles, and which is also able to be used comfortably for beauty purposes and during athletics.

The insole according to this invention is molded of materials such as elastomers of various kinds including silicone rubber, so that it is of small bulk, and accomodates itself readily to the movement of the sole to adhere closely thereto, thereby having a very good running in the region of the sole.

This invention has for another object the provision of an insole which is able to be loaded with the aid of common socks or similarly made holder.

Still a further object of this invention is to provide an insole which has good air permeability and can be washed, and further which is light in weight and low-priced.

DETAILED DESCRIPTION OF PREFERRED EMBODIMENTS

Figure 1:
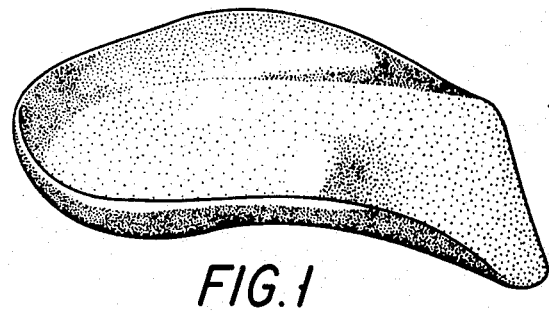
FIG. 1 is a perspective view showing an example of conventional insoles.
Figure 2:
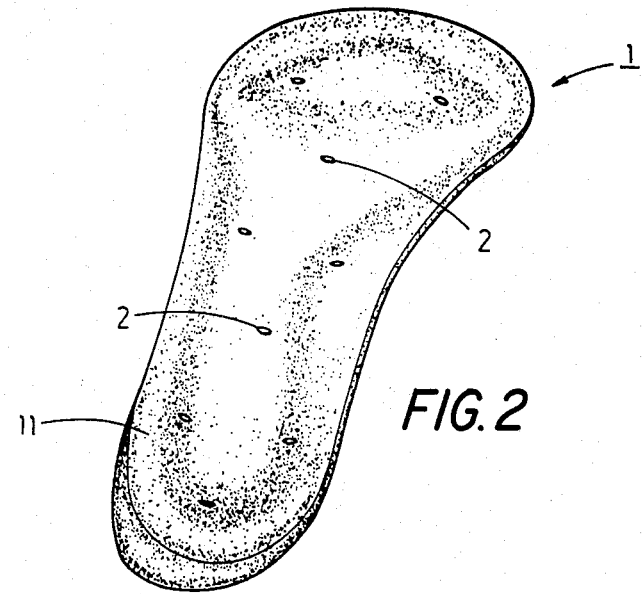
FIG. 2 is a perspective view showing an example of the insoles according to the invention.
Figure 3:
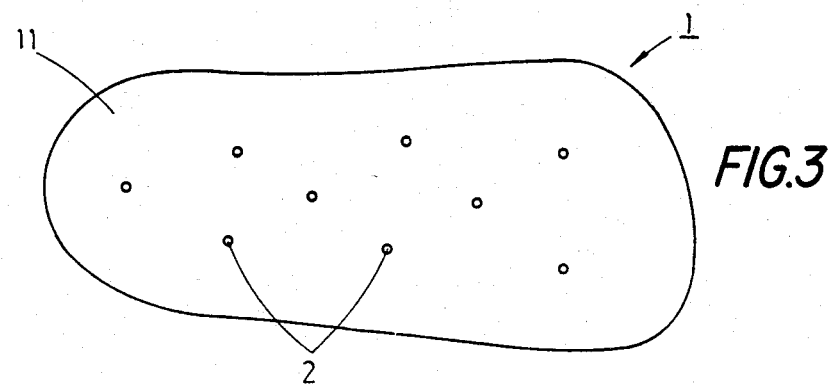
FIG. 3 is a plan view of the same insole of FIG. 2.

In FIGS. 2 and 3, there is shown an example of the insoles according to the invention. This insole (1) is an example of lateral wedge insoles (exclusively for left foot use) used for the conservative treatment of the baker leg, and so on. The upper face of the insole (1) is made in the undulating form in accord with the sole of the foot (reference numberal (31) in FIG. 5(b)), and the whole of the insole takes the form of a wedge being made thicker toward the left side (11) with the object of obtaining the expected therapeutic value. This insole is formed of elastomers such as silicone rubber, polyurethane elastomer and the like which develop gum-like elasticity under normal temperatures. Incidentally, reference numeral (2) in the figures indicates small holes for air permeation being bored through from the upper face to the lower face of the insole.

Figure 4:
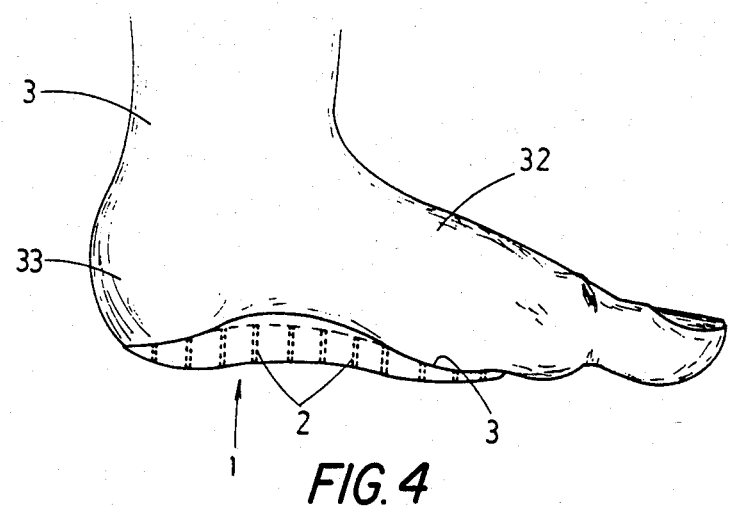
FIG. 4 is a side view of the same insole in the state of its being loaded on the foot.

Since elastomer is used as the material for this insole (1), it has flexibility, is hard to break down, has close adhesion to the sole of the foot, and has a proper degree of hardness for resistency to the load of the foot. Therefore, it becomes unnecessary for the insole to have an extra thickness for strength and to maintain its shape, or to be made largish in mass and curved on the brim with the intention of improving fit to the sole. In this way, as seen in FIG. 4, it can be made relatively less bulky on the whole in proportion to the foot (3) and also compact in geometry. On the other hand, this insole (1) has an extremely good fit to the sole with a comfortable feeling on the foot, is skidproof, and can accord satisfactorily with the movement of the sole (31). Consequently, putting on the insole (1) iseasy, and the stability of the foot is heightened, wherewith the putting on with the use of socks also become simple and easy. This was thought of as difficult or rather impossible for a long time. Such being the case, the application of this insole is possible with all types of footwear such as slippers, sandals, as well as shoes, whereby the therapeutic value can be increased. It can also be used as a cushion in the shoe. Furthermore, because of its nature of being ready to closely adhere to the footwear and sole of the foot, it can be further used as the same as above on slippers or sandals.

Figure 5A:
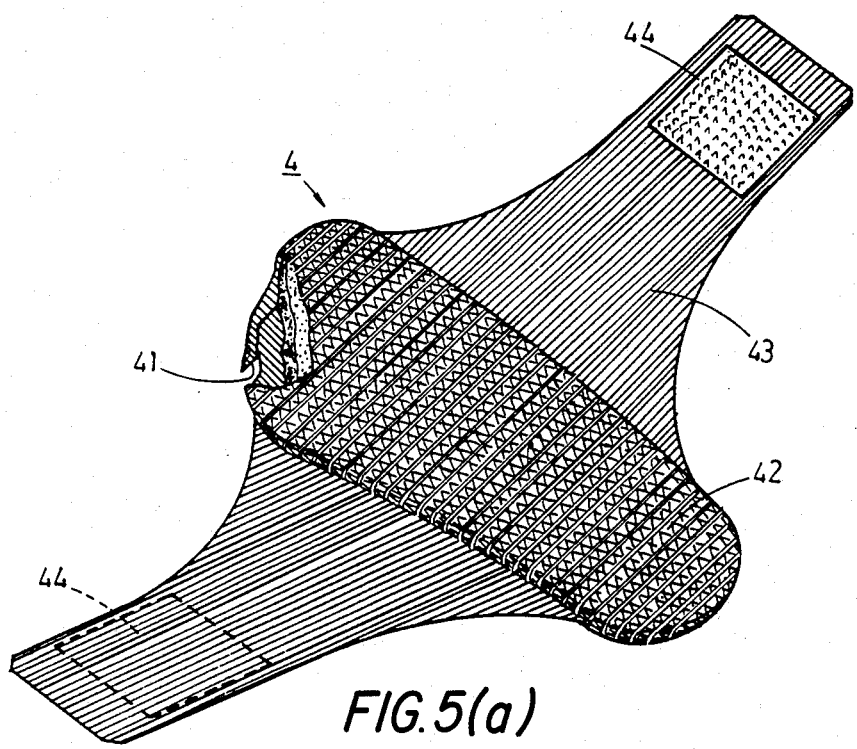
FIG. 5(a) is a side view showing an example of the holders according to the invention.
Figure 5B:
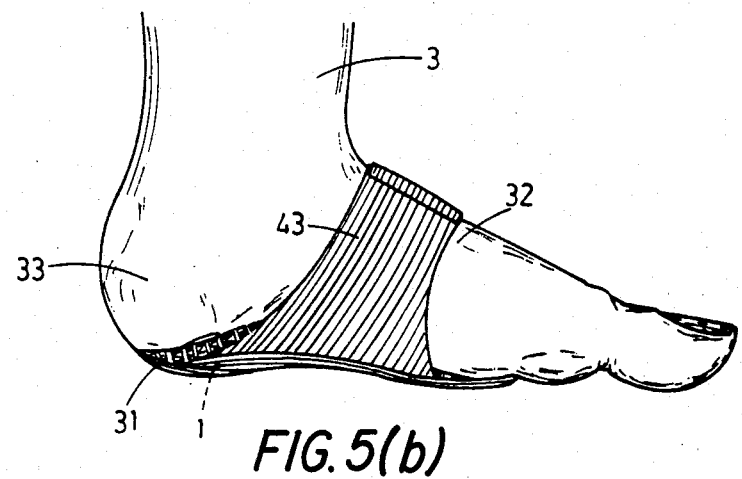
FIG. 5(b) is a perspective view in the state where the insole is held on the foot with the aid of the holder.

In connection with the above, the wearing of the insole (1) on the sole (3) may be achieved by the use of a holder (4) as shown in FIG. 5(a). This holder (4) is constructed, for example, in such a manner that band bodies (43) are attached to both sides of a bag body (42) which has an opening part (41) for taking in and out the insole (1), and that coupling means (44) are provided on both end parts of those band bodies (43). In making use of this holder, the bag body (42) is applied on the sole with the insole (1) being received within the bag body (42), and then the band bodies (43) are coupled on the instep of the foot, making them settle there stably. Materials for the bag body (42) and the band bodies (43) should have good adhesion to the sole (3) and high air permeability. To this end, cloth made of, for example, stretchy yarn, spandex, or knitted goods, may be used. For the coupling means (44) shown in the figure, face fasteners (e.g., Velcro) are used, but in addition to that, buttons, snaps, hooks, strings and others may be used.

As for the position and form of the opening (41) of the holder (4), they may be modified arbitrarily, while the band bodies (43) being separated in two in the figure may be united in a single continuous arch-shaped band, both ends of which are fixed fast on the bag body (42), by being deprived of the coupling means (44) and adding a new band body instead which is to be hung on the instep of the foot.

If using a holder (4) of this type, the insole (1) can be worn on the sole (31) very simply and stably indoors and outdoors and with any kind of footwear. In consequence, comfort is very good and the problems of putting on are eliminated. Thus, patients do not have a feeling of discomfort and uneasiness from repeated separation and contact occuring very often between the sole and the insole, because the insole (1) follows the movement of the sole. Thus, the expected therapeutic value is increased remarkably. This holder (4) can be worn under the sock because of the holder being of small bulk. Further, this holder (4) is high in air permeability since it is made of cloth or knitted goods, and it is also sanitary since it is washable.

On the other hand, the insole (1) according to this invention can also be washed without difficulty, unlike soles made of leather or cork. The insole which is provided with small holes for ventilation, as shown in the figure, is never filled with dampness due to perspiration, thus the cleanliness of the foot is preserved and an offensive smell is mitigated by large margin. These small holes for ventilation may be disposed suitably over the whole surface or to the central side of the insole. The air permeability of these small holes for ventilation is better the larger they are in size and the more they are in number. The size and number of them, however, naturally have their limits. In practice, they should be about 0.5–2 m/m in diameter and about 10–15 in number for easy cleaning.

Description will be now directed to the materials used in this invention.

The insole according to the invention is a molding of elastomer which has a gum-like elasticity at normal temperatures. Elastomers that may be used include silicone rubber, synthetic rubbers such as butadien polymer, butadien copolymer, chloroprene polymer, isobutylene polymer, and the like, polyurethane, polyisobutylene, polyethylene, and certain types of polyester, which all are non-toxic or of low toxicity. These elastomers may be mixed with various kinds of fillers, forming agents and other additives as long as they do not lose the characteristics of the elastomer and suit the utilization purpose of the insole according to the invention.

Of these elastomers, silicone rubber is one of the most preferable, because it is especially excellent in water-resisting property, thermal and low-temperature resistance, odorlessness, non-toxicity, and high tensile strength. However, silicone rubber is expensive in the form of a single substance, is bad in tensile strength, internal tearing resistance, crack resistance and others on account of its essentially weak intermolecular force and its non-crystal structure, and therefore requires a mixture of various kinds of fillers aiming at both reinforcement and increase in quantity. Furthermore, it is bad in workability, for example, it is hard to defoam the bubbles incorporated in company by the manufacture.

The inventors of the present invention, who had been manufacturing insoles with various conventionally used silicone rubber compounds, developed an ideal silicone rubber compound as material for the insole.

As the result, they found a silicone rubber compound which is low-priced, good in workability, and has an excellent foam-forming property. The excellence of this compound in foam-fitting property is preferable for reasons of being able to obtain an insole which is light-weight and good in heat-retaining property through utilizing the low defoaming property of silicone rubber.

The silicone rubber compound developed is a mixture of both inorganic filler and hydrous silicate powder with heat-vulcanized silicone rubber. In this connection, the elastomer is made by mixing only calcium carbonate as a filler with silicone rubber, keeps the fluidity, has the good workability, and the elevation of its strength is perceived, but does not greatly increase volume, but increases the specific gravity without contributing to the lowering of the production cost. On the other hand, in the elastomer wherein only hydrous silicate powder is mixed, the hydrous silicate powder is hard to disperse into silicone rubber although the light-weightness is brought about by the action of foam-formation, but fluidity is lowered remarkably, thus the workability is deteriorated. These defects have been eliminated by the present invention by mixing and dispersing both components: calcium carbonate and hydrous silicate powder into silicone rubber at predetermined certain ratio.

As inorganic fillers used in this invention, there can be used various sorts and grain sizes of calcium carbonate, magnesium carbonate, talc, aluminum hydroxide, magnesium hydroxide, calcium sulfate, calcium silicate, ground silica, clay, mica, glass beads, micro-balloon, silica balloon, and others. Preferable out of the above are the fillers which are low in oil absorption value so that the fluidity does not decrease at the time of mixing the silicone rubber, and with which a surface treatment such as the silane treatment is conducted to increase the strength of the product, especially the tearing strength, cracking resistance, and others. Most preferable is the surface-reactive calcium carbonate whose grain surface has been activated by a silane coupling agent. Further, one having a specific gravity as low as possible is preferable to make the product light-weight.

As for hydrous silicate powder, it fulfills its function such as the actualization of high strength of the product or the reduction of production cost as an inorganic filler, and further it can make minute bubbles uniform by the action of water being contained therein, playing an important role in making the product light-weight and in forming the product. In this way, a foaming agent belonging to the organic group is not needed. In practice, white carbon is used which is one of the noncrystal hydrous silicate powders. In addition, any pigment and other additives can be freely mixed if the product has the expected object properties.

The preferable compounding ratio of these components is 5–75 parts (by weight: hereinafter the same) of an inorganic filler and 5–30 parts of hydrous silicate powder together with 100 parts of heat-vulcanized silicon rubber and 10 parts of a conventional silicone rubber vulcanizing agent. When mixing more than 75 parts of the inorganic filler, the fluidity drops and the workability becomes poor and when less than 5 parts, small bubbles in company with the foam-formation are not incorporated within, so that blow-off (bumping) holes occur unpreferably. Especially preferable is the limits of 10–50 parts of inorganic filler. On the other hand, in the case of hydrous silicate powder, when mixing more than 30 parts of it, the fluidity drops considerably, and when less than 5 parts, the foam-formation is not satisfactorily performed, and sometimes the one-sided formation is unpreferably generated. Especially preferable is the limits of 10–20 parts of hydrous silicate powder.

Figure 6:
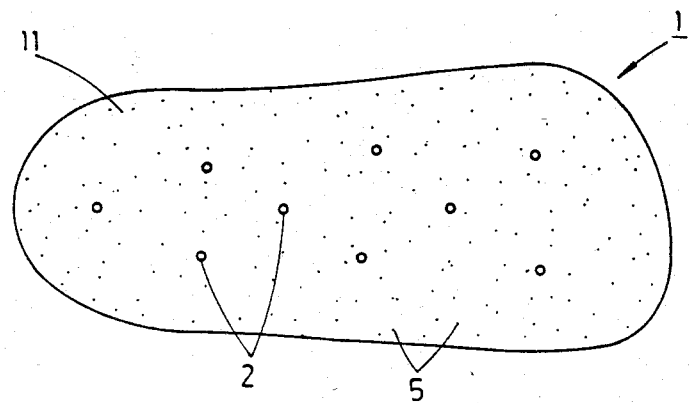
FIG. 6 is a plan view showing a modification of the insoles according to the invention.

By way of example, as a start 10 parts of the vulcanizing agent is mixed and stirred thoroughly with 100 parts of the heat-vulcanized silicone rubber (a colorless, transparent liquid). Next, when commingling 25 parts of calcium carbonate being previously surface-treated by silane coupling agent, and 15 parts of white carbon which is noncrystal hydrous silicate powder of high purity, there can be obtained a slurry of high fluidity. After being poured into a mold, this slurry is heated at about 100° C. in a thermostatic oven for about one hour to harden. The object released from the mold is a hardened body which is light-weight and contains many minute bubbles scattered uniformly on the whole surface, as shown in FIG. 6. This hardened body, that is the insole (1) is warm and exhibits excellent internal tearing resistance and cracking resistance.

The silicone rubber compound according to the invention has the proper fluidity and the foam-forming property, whereby it can dispense with the need for the defoaming process which has been most difficult heretofore in making use of the foam-formation but also elevate the working efficiency at a large margin. The product obtained is also light-weight and excellent in internal tearing strength and cracking resistance. Furthermore, it increases warmth of the foot by involving the small balls in itself, thereby minimizing cold feet in winter. Moreover, the mixing of inorganic fillers and the foam-formation enable the production cost to be cut down sharply compared with conventional products. All things considered, it may be said that the insole of this invention is the most suitable one as a therapeutical means which is to be worn on the human body because all the component materials are harmless and non-toxic.

Figure 7:
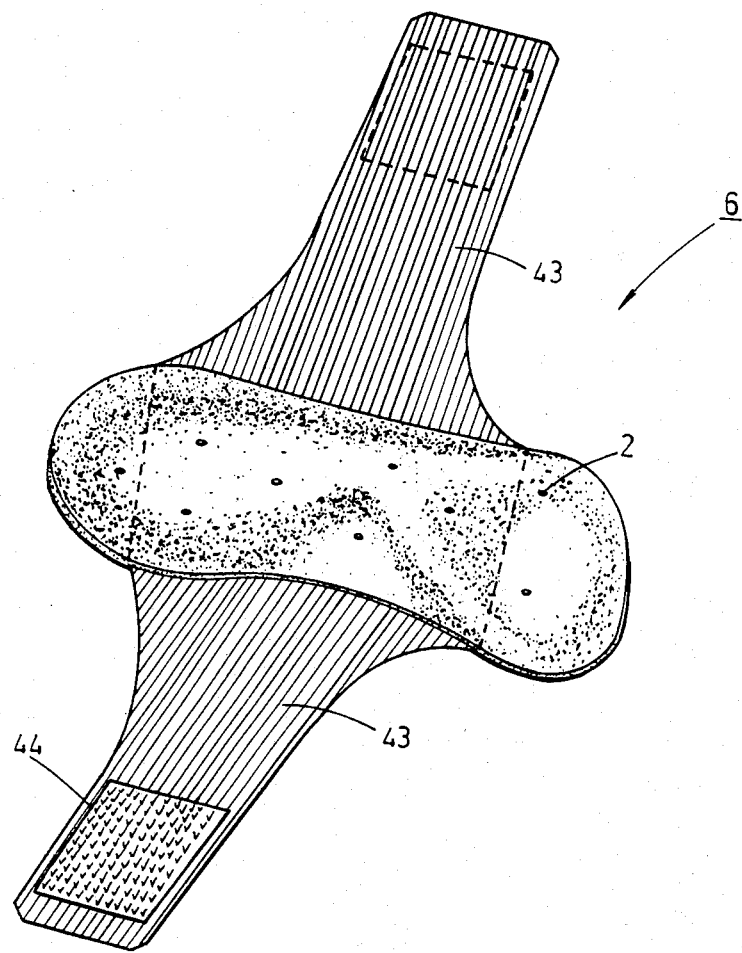
FIG. 7 is a perspective view showing a modification of the holder (in this case, along with the insole loaded thereon).

Polyurethane elastomer is also a desireable material. This material is also easy to mold and adapted to the short-run production of a large variety of descriptions, and has the excellent properties such as the wearability, high internal tearing strength and others, and further has a wide range of hardness, as a result of which it is possible to easily obtain a material suitable for the insole. In comparison with silicone rubber, it is cheap in unit cost, and has the highest adhesiveness of the other substances. Accordingly, as seen in FIG. 7, it is possible to make up an insole (6) with a holder, simple in constructioon, which is molded by embedding the band body (numeral (43) in FIG. 5) into the before-described insole (1) itself.

As described above, the insole according to the invention is integrally molded by the use of elastomer having gum-like elasticity, is of small bulk, closely follows the movement of the sole of the foot while closely adhering thereto, and thereby is able to become very satisfactorily accustomed to the sole part. What is more, it is possible for it to be worn with the aid of socks and other simple holders, and to increase its therapeutic value. For insoles, except the lateral wedge insole described in the foregoing examples, there are also different kinds of insoles for medical use such as the medical wedge insole used for the conservative treatment of baker legs, the arch support used for the treatment of fat feet, the metatarsal support, and the insole used to supplement one's stature. These insoles all display an excellent effect.

Also, the insoles provided for the temporal use such as the insole for the supplement of stature for beauty purposes or the inclining insole for athletics have such large advantages as being able to be loaded on the sole simply and securely and improve the stability of the foot.

Insoles which may be made according to this invention include, in addition to the one covering the whole of the sole from near the metatarsus to the instep of the foot, as shown in the figures, also include the partial ones which are restrictedly applied, for example, to the platar arch or the metatarsal part of the foot. It may also be desireable to generate bubbles throughout the whole body of the insoles within the range of the hardness sufficient to achieve the expected object, which bubbles perform air permeation. It may also be desireable to color the insoles with different tints. Then people, particularly women, will be more agreeable to wearing them since, if they are tinted flesh color, they will not be obvious under stockings.

What is claimed is:

1. An insole of wedge-shaped, irregular or curved section which insole comprises:
    inorganic filler in the range of five to seventy-five parts;
    hydrousilicate powder in the range of five to thirty parts;
    heat vulcanized silicone rubber of substantially one hundred parts; and
    silicone rubber vulcanizing agent of substantially ten parts.

2. The insole according to claim 1 wherein said inorganic filler is in a range of ten to fifty parts and said hydrousilicate powder is in the range of ten to twenty parts.

3. The insole according to claim 2 wherein said inorganic filler comprises twenty-five parts of silane surface treated calcium carbonate and hydrausilicate powder comprises five parts of white carbon non-crystal and hydrasylicade powder.

4. The insole according to claims 1, 2 or 3 including a plurality of small holes for ventilation.

5. The insole according to claims 1, 2 or 3 including a uniform incorporation of minute bubbles throughout said insole.

6. The insole according to claims 1, 2 or 3 further including a band body intergally molded with said insole for wearing said insole on the sole of the foot.

7. The insole according to claims 1, 2 or 3 wherein said insole is skin-colored.

* * * * *